United States Patent [19]

Mueller, Jr.

[11] Patent Number: 4,601,701
[45] Date of Patent: Jul. 22, 1986

[54] MULTI-PURPOSE MULTI-LUMEN CATHETER

[75] Inventor: Richard L. Mueller, Jr., Athens, Tex.

[73] Assignee: Argon Medical Corp., Athens, Tex.

[21] Appl. No.: 705,178

[22] Filed: Feb. 25, 1985

[51] Int. Cl.⁴ .............................................. A61M 5/00
[52] U.S. Cl. ..................................... 604/83; 604/256; 604/280
[58] Field of Search ............ 604/280, 283, 284, 82–85, 604/89, 236, 249, 256, 258, 164, 165, 169, 33

[56] References Cited

U.S. PATENT DOCUMENTS

| | | | |
|---|---|---|---|
| 3,081,770 | 3/1963 | Hunter | 604/33 X |
| 4,069,814 | 1/1978 | Clemens | 604/83 |
| 4,509,507 | 4/1985 | Yabe | 128/4 |
| 4,526,573 | 7/1985 | Lester et al. | 604/33 |

Primary Examiner—Stephen C. Pellegrino
Attorney, Agent, or Firm—Lawrence S. Levinson; Sanford J. Asman

[57] ABSTRACT

The catheter includes multiple lumens which connect to a single mixing chamber at the catheter hub. Each of the multiple lumens is connected both to the mixing chamber and to a port connected to a catheter connector. By selecting a plug of suitable length, one or more of the side ports connected to the central mixing chamber can be plugged whereby the connection from that particular side port will be prevented from going into the mixing chamber. Accordingly, it is possible to have a single catheter connection into the mixing chamber which connects to multiple lumens of the catheter without any additional plumbing requirements.

3 Claims, 4 Drawing Figures

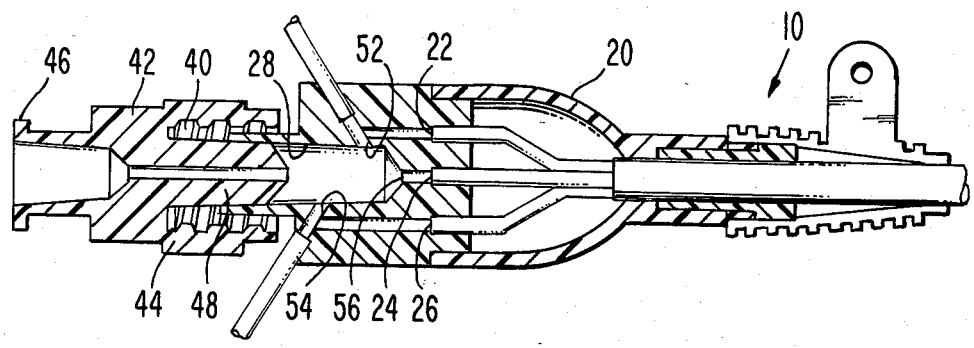
Fig_2_
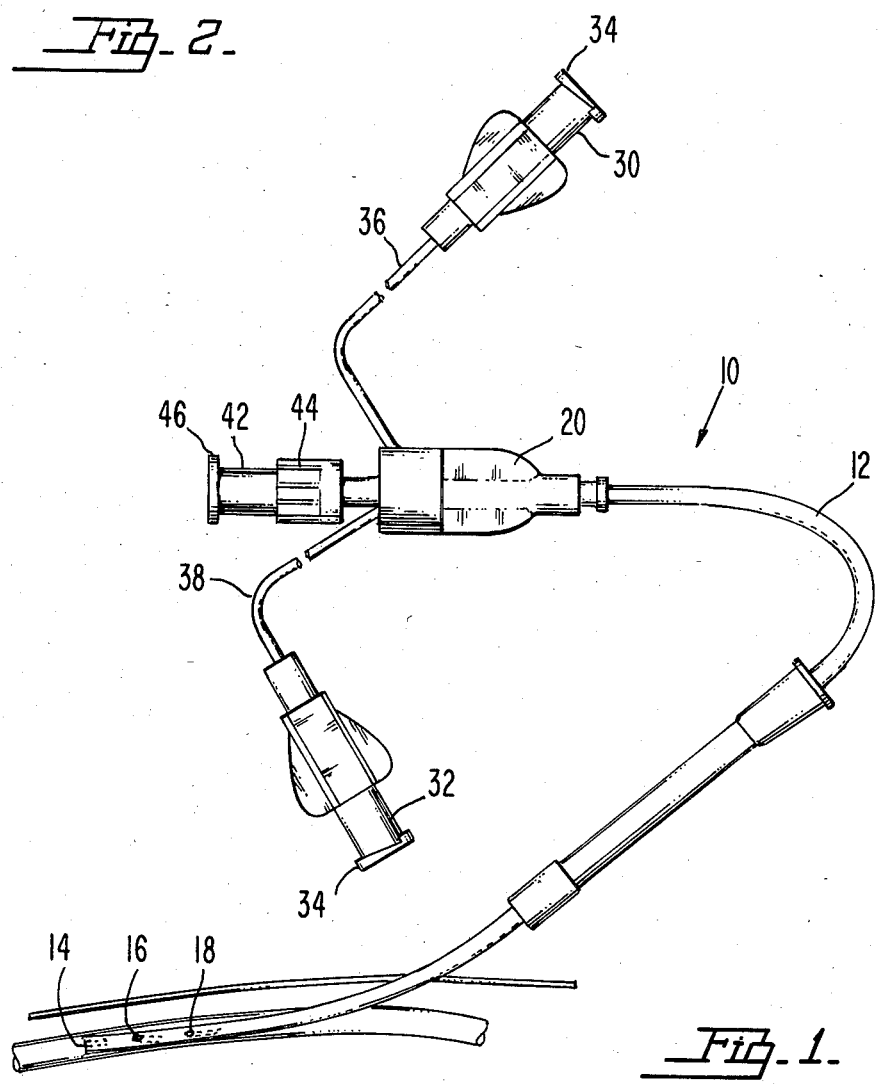
Fig_1_

MULTI-PURPOSE MULTI-LUMEN CATHETER

BACKGROUND OF THE INVENTION

The present invention relates to a venus catheter device. In particular it relates to a single catheter device which may be used either to infuse multiple fluids through multiple lumens, or, alternatively, to use multiple lumens and infuse through some or all of them simultaneously.

Conventional venus catheter devices use either a single lumen or multiple lumens. Those which were known heretofore which had multiple lumens had a corresponding number of inlet ports to the lumens, i.e. three inlet ports for three lumens. Such catheters are used in medical applications to introduce or extract fluids from a patient. In particular, multiple lumen catheters are designed to take advantage of having several different lumens within a single catheter body. Multiple, separate lumens in one catheter reduce the number of separate catheters requiring separate puncture sights to the patient. In addition, multi-lumen catheters offer isolated lumens for fiber optic and electronic units. A disadvantage of multiple lumen catheters of the type heretofore known is that each lumen must be reduced in size, and, therefore, flow rate, in order to have multiple lumens fit within a single external diameter. Accordingly, current designs for multi-lumen catheters sacrificed flow rate for the multiple lumens.

SUMMARY OF THE INVENTION

In accordance with the present invention, a multi-lumen catheter having a multi-lumen, multi-function valve is described. The multi-function valve is used in conjunction with a Luer nose whose length determines the number of lumens which are connected to a single port. In addition, a mixing chamber is provided, whereby multiple lumens may be used to deliver fluids which were mixed in the mixing chamber.

BRIEF DESCRIPTION OF THE DRAWING

In the Drawing:

FIG. 1 is a side view of the present invention showing a catheter inserted into a patient; and FIGS. 2-4 are cross-sectional views of the multi-lumen catheter of FIG. 1 showing the catheter hub with a number of different Luer nose fittings whereby the number of lumens connected to the mixing chamber may be selected.

DETAILED DESCRIPTION OF THE PREFERRED EMBODIMENT

Figure 3:
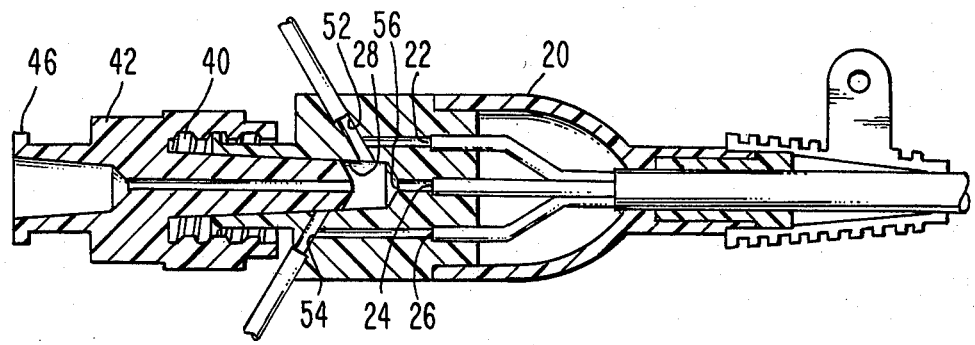

Referring generally to FIG. 1, the multi-lumen catheter 10 of the present invention is shown. In the embodiment 10 of FIG. 1, the catheter 10 comprises a tube 12 having three distinct, internal lumens which terminate in openings 14, 16, 18, respectively. The proximal end of the catheter 10 is connected to a hub assembly 20 which is illustrated in detail in FIGS. 2-4.

Referring to FIG. 2, the hub assembly 20 includes openings 22, 24, 26 which enter the respective lumens of the catheter 10. The various openings 22, 24, 26 are connected to a central mixing chamber 28. The individual catheter adapters 30, 32, shown in FIG. 1, each have connectors 34, which are Luer type connectors in the preferred embodiment 10. The individual catheter adapters 30, 32 are connected to the central mixing chamber 28 by means of tubes 36, 38, having internal cross-sectional areas substantially the same as those of the lumens of the catheter 10. There is a connector 40 on the catheter hub 20.

Figure 4:
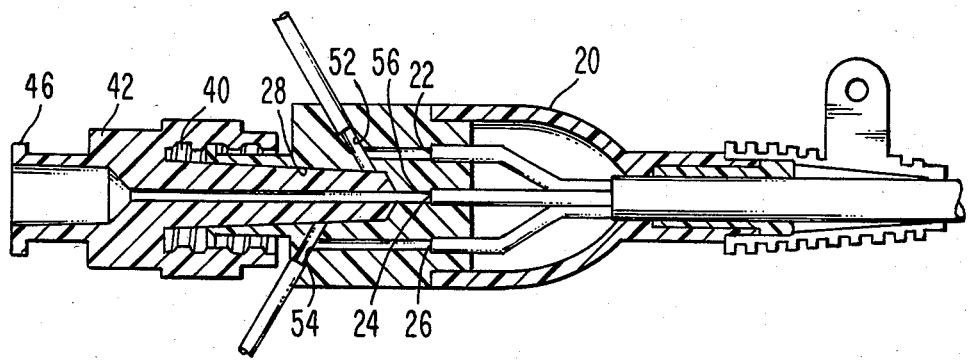

A Luer nose 42 is connected to the connector 40. The Luer nose 42 has an internal connector 44 which attaches to the connector 40 on the catheter hub 20. The Luer nose 42 also includes a Luer type connector 46 which may be used to attach a fluid transfer device to the Luer nose 42. The Luer nose 42 includes a plug 48 which has a length selected to provide access to one or more of the lumen entries 22, 24, 26 through mixing chamber entry ports 52, 54, 56, respectively, as shown in FIGS. 2-4. Thus, by using a Luer nose 42 having a plug 48 with the appropriate length, one or more of the entry ports 52, 54 entering the mixing chamber 28 may be closed off (See FIGS. 3 and 4). Alternatively, if all three lumens 22, 24, 26 are to be used to deliver a single fluid, then a short Luer nose 48 can be used as shown in FIG. 2. As will be obvious to those skilled in the art, if the Luer adapters 30, 32 are not used in a particular procedure then they should be sealed to prevent air from entering or fluids from exiting therefrom.

In accordance with the present invention, the doctor has the versatility to choose separate lumens or a single, higher flow lumen by combining the multi-lumens of the catheter 10. Such combinations can be selected after the catheter 10 has been placed into a patient whereby, if separate lumens are required in one procedure and multiple lumens are required in a subsequent procedure, there is no need to remove and replace the catheter 10. In addition, the mixing chamber 28 can be used to mix or dilute drugs from different input adapters prior to their entering the patient.

While the present invention has been described with reference to a multi-lumen catheter having three lumens, other numbers of lumens can be readily constructed without departing from the spirit or scope of the present invention.

I claim:

1. A multi-lumen catheter comprising:
   (a) a catheter having at least two lumens which open at the distal end thereof;
   (b) a hub at the proximal end of said catheter, said hub including a central mixing chamber into which the individual lumens of said catheter are connected, channel means within said hub for connecting at least one of said lumens both to said mixing chamber and to an external fluid adapter;
   (c) external connecting means for connecting an external fluid transfer device to each of said channel means; and
   (d) means for selectively closing off said external connecting means from said central mixing chamber and for connecting said external fluid transfer device selectively to said central mixing chamber of at least one of said lumens.

2. The multi-lumen catheter of claim 1 wherein said means for selectively closing off is in the form of a plug having a length selected to be capable of closing off selected ones of said channel means.

3. The multi-lumen catheter of claim 2 wherein said central mixing chamber is open at one end to receive a plug-like fitting and said channel means comprise openings which extend from said central mixing chamber to each of said individual lumens, said openings also being in communication with said external connecting means, wherein said means for selectively closing off is in the form of a plug which has a length adapted to seal selected ones of said openings.

* * * * *